US010080565B2

(12) United States Patent
Pastorelli et al.

(10) Patent No.: US 10,080,565 B2
(45) Date of Patent: *Sep. 25, 2018

(54) SURGICAL STAPLING INSTRUMENT

(71) Applicant: ETHICON ENDO-SURGERY, INC., Cincinnati, OH (US)

(72) Inventors: Alessandro Pastorelli, Rome (IT); Michael A. Murray, Bellevue, KY (US); William Bruce Weisenburgh, II, Maineville, OH (US); Federico Bilotti, Latina (IT); Laszlo Csiky, Urom (HU); Todd Phillip Omaits, Liberty Township, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 355 days.

This patent is subject to a terminal disclaimer.

(21) Appl. No.: 14/697,659

(22) Filed: Apr. 28, 2015

(65) Prior Publication Data
US 2015/0230797 A1 Aug. 20, 2015

Related U.S. Application Data

(63) Continuation of application No. 13/430,745, filed on Mar. 27, 2012, now abandoned, which is a
(Continued)

(51) Int. Cl.
*A61B 17/04* (2006.01)
*A61B 17/10* (2006.01)
(Continued)

(52) U.S. Cl.
CPC .......... *A61B 17/105* (2013.01); *A61B 17/068* (2013.01); *A61B 17/115* (2013.01); *A61B 17/1114* (2013.01); *A61B 17/32053* (2013.01)

(58) Field of Classification Search
CPC .............. A61B 17/068; A61B 17/1155; A61B 2017/07214; A61B 2017/07278; A61B 17/105
(Continued)

(56) References Cited

U.S. PATENT DOCUMENTS 3,771,526 A 11/1973 Rudie
4,289,133 A 9/1981 Rothfuss
(Continued)

FOREIGN PATENT DOCUMENTS

EP 0137685 B1 6/1988
EP 0517488 B1 4/1996
(Continued)

OTHER PUBLICATIONS

European Search Report dated Dec. 12, 2006; European Application No. 06116804.3.
(Continued)

*Primary Examiner* — Robert Long

(57) ABSTRACT

A surgical stapling instrument (1) comprises a staple fastening assembly (4) in the distal region of said instrument, the staple fastening assembly (4) including a cartridge device (8) which comprises at least one closed row (17, 18) of staples and defines a wavy distal end surface (14), and an anvil (9) which defines a wavy proximal staple forming surface (20) substantially matching the distal end surface (14) and which is adapted to cooperate with the cartridge device (8) for forming the ends of the staples exiting from the cartridge device (8), wherein the distal end surface (14) and the staple forming surface (20) have a globally wavy shape including two opposite peaks (21) and two opposite valleys (22) angularly spaced at about 90° from the adjacent
(Continued)

peaks (21) and in that said two-peaks-two-valleys wavy shape is formed by a stepped configuration of said surfaces (14, 20).

15 Claims, 7 Drawing Sheets

Related U.S. Application Data continuation of application No. 12/307,751, filed on Jan. 7, 2010, now Pat. No. 8,413,870.

(51) Int. Cl.
    *A61B 17/11*     (2006.01)
    *A61B 17/115*     (2006.01)
    *A61B 17/068*     (2006.01)
    *A61B 17/3205*     (2006.01)

(58) Field of Classification Search
    USPC ............ 227/175.1–182.1; 606/139, 142, 143
    See application file for complete search history.

(56) References Cited

U.S. PATENT DOCUMENTS

| | | | |
|---|---|---|---|
| 5,205,459 A | 4/1993 | Brinkerhoff et al. | |
| 6,193,129 B1 | 2/2001 | Bittner et al. | |
| 6,978,922 B2 | 12/2005 | Bilotti et al. | |
| RE40,237 E * | 4/2008 | Bilotti ................. | 227/176.1 |
| 7,422,138 B2 | 9/2008 | Bilotti et al. | |
| 7,749,235 B2 * | 7/2010 | Sheets, Jr. ........ | A61B 17/00491 606/139 |
| 7,753,249 B2 * | 7/2010 | Sonnenschein .... | A61B 17/0686 227/175.1 |
| 2003/0009193 A1 * | 1/2003 | Corsaro ............... | A61B 17/072 606/207 |
| 2003/0178465 A1 | 9/2003 | Bilotti et al. | |
| 2004/0004105 A1 * | 1/2004 | Jankowski .......... | A61B 17/072 227/176.1 |
| 2005/0189397 A1 * | 9/2005 | Jankowski .......... | A61B 17/072 227/176.1 |
| 2007/0114261 A1 * | 5/2007 | Ortiz .................... | A61B 17/064 227/175.1 |
| 2010/0108740 A1 * | 5/2010 | Pastorelli ............ | A61B 17/1114 227/178.1 |
| 2011/0017800 A1 * | 1/2011 | Viola ................... | A61B 17/115 227/175.1 |
| 2012/0325893 A1 * | 12/2012 | Pastorelli ............ | A61B 17/072 227/177.1 |

FOREIGN PATENT DOCUMENTS

| | | | |
|---|---|---|---|
| EP | 0698376 B1 | 7/2003 | |
| EP | 1254636 B1 | 10/2004 | |
| EP | 1754445 A2 | 2/2007 | |
| EP | 1875870 A1 * | 1/2008 | ......... A61B 17/1114 |
| EP | 1875870 B1 | 2/2009 | |
| EP | 1316290 B1 | 2/2012 | |
| JP | 2003199749 A | 7/2003 | |
| JP | 2003521301 A | 7/2003 | |
| WO | WO 01/54594 A1 | 8/2001 | |

OTHER PUBLICATIONS

European Search Report dated Apr. 16, 2007; European Application No. 06116804.3.
International Search Report dated Jul. 7, 2006; International Application No. PCT/EP2007/056055.
Auto Suture 2006 Product Catalog, Tyco Healthcare, 2006 (103 Pages).

* cited by examiner

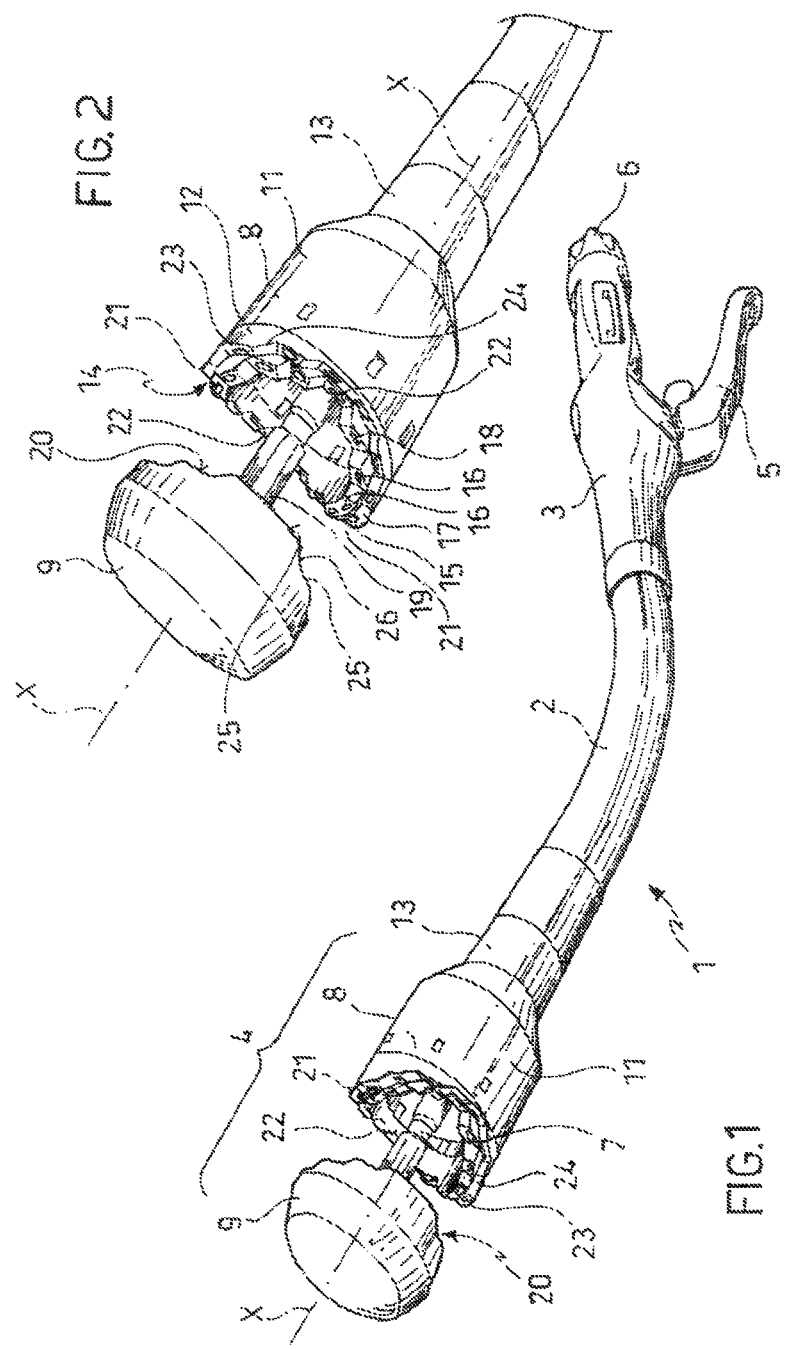

SURGICAL STAPLING INSTRUMENT

The invention relates to a surgical stapling instrument, which can be used for applying surgical staples or clips to tissue. And particularly the invention relates to an intraluminal surgical stapling instrument for the creation of an anastomosis.

Surgical stapling is known in the art as a quick and efficient way of joining and repairing tissue and has become not only an acceptable but a preferred alternative to suturing.

The known intraluminal surgical stapling instruments typically comprise an elongate shaft having a proximal actuating mechanism and a distal staple fastening assembly mounted to the shaft. The staple fastening assembly typically comprises a staple cartridge device containing a plurality of staples arranged in a circular closed array. A circular cutting knife having a closed cutting edge is contained within the cartridge device and is positioned such that there is at least one closed row of staples on the outside of the cutting edge. The knife can be advanced in an axial distal direction during operation. A trocar shaft extends distally from the cartridge device and is axially movable with respect to the latter. An anvil is detachably mounted to the trocar shaft and comprises a staple forming surface facing the distal end surface of the cartridge device and adapted to form the ends of the staples pushed by a staple driving device against the anvil. The distance between the cartridge end surface and the anvil staple forming face can be varied by an adjustment mechanism mounted to the proximal end of the trocar shaft and configured to move the trocar shaft together with the anvil with respect to the staple cartridge device. The actuating mechanism typically links the staple driving operation to the knife advancing operation such that the tissue contained between the staple cartridge device and the anvil is simultaneously stapled and cut when the actuating mechanism is triggered by the surgeon.

Generally, in the performance of an intraluminal anastomosis, two pieces of lumen or tubular tissue, e.g. intestinal tissue, are joined together by a closed row of staples. In performing the anastomosis with a surgical stapling instrument, the anvil is placed in the proximal end of the distal lumen or tissue portion (from a surgeons viewpoint) and the cartridge device is placed in the distal end of the proximal lumen or tissue portion to be joined. The placement of anvil and cartridge device can be done by inserting them through entry ports cut into the corresponding lumen by the surgeon or by inserting them endoscopically, e.g. transanally through the rectum. The lumens or tissue portions destined to be joint in anastomosis can be tied to the anvil shaft and/or trocar shaft using a suture or other conventional tying technique. Thereafter, the anvil shaft is attached to the trocar shaft of the staple fastening assembly (cartridge device) and the gap between the cartridge device and the anvil is closed, thereby clamping the proximal and distal tissue portions together in the gap. Upon actuation of the intraluminal stapling device one or more closed rows of staples are driven out of corresponding staple guide slots of the cartridge device. The staples are driven through the distal and proximal tissue portions and formed against an array of staple forming grooves of the anvil, thereby joining the tissue portions and forming a tubular pathway.

Simultaneously, as the staples are applied and formed, the circular knife is advanced distally to cut the excess tissue adjacent to the inner annular row of staples. Then, the edge joined by the closed row of staples is unclamped by advancing the trocar shaft distally with respect to the cartridge device to move the anvil away from the cartridge device. The stapling instrument is then withdrawn from the anastomotic site by pulling the anvil proximally through the anastomotic orifice defined by the annularly stapled tissue edges.

Although the use of the known surgical stapling instruments is very beneficial and greatly facilitates the performance of an anastomosis, it involves some problems. Often it is difficult to retract the instrument from the site of the operation, because it is difficult to withdraw the anvil through the anastomotic opening defined by the closed row of staples, which is somewhat stiff. Moreover, after the operation, the incidence of clinical stenosis at the site of the anastomosis is not rare.

In order to overcome these known deficiencies, it is proposed in WO 01/54594 A1 to arrange the closed row of staples in a wavy shape. In this way, the line along which the staples of the closed row are arranged has a greater total length than the projection of this line onto a plane. Consequently, the length of an anastomosis seam is greater than that of an anastomosis performed by means of a conventional stapling instrument. Because of this increased length, the anastomotic site can assume a larger diameter and is more flexible, so that the anvil can be easier moved through the anastomotic opening. Additionally, the resulting larger anastomosis lumen will alleviate the incidence of clinical complications.

Nonetheless the wavy shape of the staple arrangement has some drawbacks. For optimum performance of the stapling instrument, the individual staples are expelled from the cartridge device in a direction perpendicular to the local slope of the wavy shape, which generally is not parallel to the longitudinal axis of the instrument, requiring a complex staple drive device. Moreover, due to the oblique orientation of the staple driving direction with respect to the anvil approximation direction (axial direction of the stapler) the alignment of the staple-forming grooves at the anvil and the staple guide slots of the cartridge device varies undesirably with any variation of the distance between the cartridge device and the anvil, thereby limiting the use of the stapler to only one thickness of tissue to be joined in anastomosis.

Moreover, since the length of the wavy stapled seam can be increased only by increasing the number of waves along the circular staple line and by increasing the amplitude (axial extension) of the waves, the application of wavy circular staplers encounters some limits linked to the physiological peculiarities of the body tissue. By increasing the number of waves (at a given amplitude) along the staple line the gradient of the inclination or flexure of adjacent tissue portions is increased to an extent which might lead to tissue trauma or local rupture. On the other hand, using a staple line having only one single sinusoidal wave, the amplitude of the wave, i.e. the axial distance between the valley and the peak of the single wave, needs to be very high in order to obtain the desired increase of the length of the stapled seam. Since some tubular organs of the human and animal body, particularly the intestine, have an unilateral blood supply, an anastomosis with a great longitudinal extension with respect to the lumen might leave some regions of tissue completely isolated from blood supply, leading to necrosis.

The object of the invention is to provide a surgical stapling instrument for performing an anastomosis, which reconciles the contrasting requirements of maximizing the length of the stapled seam, minimizing the tissue trauma and reducing the complexity of the staple drive device. A further object of the invention is to provide a surgical stapling instrument being adaptable to different tissue thicknesses.

These objects are achieved by a surgical stapling instrument having the features of claim 1. Advantageous embodiments and variants of the invention follow from the dependent claims.

The surgical stapling instrument according to the invention comprises a frame having a body portion and a handle as well as a staple fastening assembly in the distal region of the instrument. The staple fastening assembly includes a cartridge device housing at least one closed row of staples and defining a wavy distal end surface, and an anvil defining a wavy staple forming surface which matches the wavy distal end surface. The anvil is movable relative to the cartridge device and is adapted to cooperate with the cartridge device for forming the ends of the staples exiting from the cartridge device. A moving device is adapted to move the anvil relative to the cartridge device. A staple driving device is adapted to drive the staples out of the cartridge device towards the anvil. A knife, which has a closed cutting edge, is contained within the cartridge device and is positioned such that there is at least one closed row of staples radially on the outside of the cutting edge. A knife actuating device is adapted to move the knife towards the anvil.

According to the invention, both the distal end surface and the staple forming surface have a wavy shape including two opposite peaks and two opposite valleys angularly spaced at about 90° from the adjacent peaks and have a stepped or otherwise offset configuration in order to create the two-peaks-two-valleys wavy shape.

The stepped surfaces are composed of a series of lands and risers, wherein the lands are substantially perpendicular to the longitudinal axis of the staple fastening assembly and the exit openings of the staple guide slots as well as the staple forming recesses are advantageously defined in the lands.

The stepped surface configuration "oscillates" about the generally two-peaks-two-valleys wavy shape configuration, thereby further increasing the length of the stapled seam with respect to the dimensions of the stapling device and without substantially increasing the overall axial extension of the anastomosis along the lumen. Moreover, the stepped configuration and the orientation of all the step lands perpendicular to the longitudinal axis allows to arrange all staples parallel to the staple drive direction of the staple drive device, thereby reducing the force necessary to penetrate the tissue and clinch the staples against the staple forming surface of the anvil.

Advantageously, the staples are arranged in the cartridge device along a wavy line including two opposite peaks and two opposite valleys angularly spaced at about 90° from the adjacent peaks, wherein the line along which the staples are arranged is substantially parallel to the corresponding distal end surface of the cartridge device. Preferably the projection of the cartridge distal end surface and the staple forming surface and the projection of the staple line onto a plane perpendicular to the longitudinal axis of the staple fastening assembly are circular.

Hence, the tissue interfaces of the surgical stapling instrument have a greater total extension than comparable planar or smooth wavy tissue interfaces. The particular shape with two opposite peaks and two opposite valleys angularly spaced at about 90° from the adjacent peaks consents to obtain an increased length of the stapled seam compared to traditional circular staplers without unnecessarily increasing the gradient of tissue flexure and the total longitudinal extension of the anastomosis along the lumen, thereby reducing the risk of trauma and tissue rupture. The length of the stapled seam is further increased by the locally stepped or offset surface configuration of the cartridge end surface and the staple forming surface which "oscillates" about the two-peaks-two-valleys wavy shape. This superimposition of two wave patterns (the global general wave and the local steps), apart from increasing the length of the stapled seam without increasing substantially the longitudinal extension of the anastomosis, consents further to align the steps, and hence the direction of the guide slots housing the staples, parallel to the longitudinal axis of the staple fastening assembly, which in turn allows the use of a simple and sturdy staple drive device.

According to an important aspect of the invention, the axial distance between the peaks and the valleys of the distal end surface and the mating staple forming surface is preferably less than 20 mm, yet preferably less than 10 mm. This dimensioning will further reduce the risk of tissue necrosis due to blood supply insufficiency.

In accordance with a further aspect of the invention, the staple fastening assembly is dimensioned in a manner that at least the external circumference of the anvil is less or approximately equal to the total length of the two-peaks-two-valleys stepped surfaces along the staple line. A very good compromise between the lumen diameter requirement and the requirement of minimizing tissue tensioning during withdrawal of the stapler from the anastomotic site has been obtained by selecting the ratio of the outside circumferential length of the anvil (and preferably also that of the staple cartridge device) to the staple line length in a range of 0.95 to 1.02.

Turning again to the general two-peaks-two-valleys wavy shape of the distal end surface and the staple forming surface, this shape can be obtained by different geometric constructions. A regular sinusoidal wave pattern leads to a gradual change of the gradient of flexure of the tissue along the staple line. A zig-zag shape with smoothed corners results in a concentration of the tissue flexure in the regions of the opposite peaks and valleys and in substantially flat intermediate regions between respectively a peak and a valley, in which no substantial tissue flexure occurs. Alternatively, the distal end surface might be advantageously defined by two planes which intersect along a diameter of the circular staple cartridge device and the staple forming surface might be advantageously defined by two planes which intersect along a diameter of the anvil. In this case it is advantageous to round the zone of intersection of the two half-planes. This would lead to substantially fish-mouth shaped surfaces.

Because of the above described geometry of the tissue clamping surfaces and the staple line of the surgical stapling instrument, the anastomotic site can assume a larger diameter and is more flexible, so that the anvil can be easily removed through the opening created by the knife, and the surgical stapling instrument can be retracted more easily. Additionally, incidence of clinical complications will be reduced.

Moreover, thanks to the perpendicular orientation of the lands of the single steps (which define the exit openings of the staple guide slots) with respect to the longitudinal axis of the staple fastening assembly, the pointed ends of staples exiting from the cartridge device stay aligned to the staple-forming grooves provided at the anvil, irrespective of the actual distance between the anvil and the cartridge device or the thickness of the tissue clamped therebetween.

Whereas it is conceivable that the knife has a conventional (cylindrical) basic shape with a circular cutting edge, in a preferred version of the invention the line defining the cutting edge of the knife has a generally wavy two-peakstwo-valleys or fish-mouth shape (having a circular projection onto a plane perpendicular to the longitudinal axis of the staple fastening assembly). The cutting edge is preferably defined by a series of steps "oscillating" about its wavy shape and parallel to the line along which the row or rows of staples are arranged. With such a design, the knife has to be moved only by a very short distance in order to completely cut the tissue clamped between the cartridge device and the anvil.

In an advantageous version of the invention, the staple fastening assembly is detachably mounted in the distal end region of the body portion. This enables, e.g., the staple fastening assembly to be exchanged during the surgical operation or to be designed as a disposable part (whereas the frame including a major part of the mechanical components is sterilizable and reusable). Moreover, the cartridge device can comprise a removable cartridge containing the staples, such that, e.g., an empty cartridge can be replaced by a fresh one, if required, or the cartridge device can be designed as a re-usable component.

These and other features and advantages of the present invention shall be made apparent from the accompanying drawings and the description thereof, which illustrate an embodiment of the invention and, together with the general description of the invention given above and the detailed description of an embodiment given below, serve to explain the principles of the present invention.

FIG. 1 is a perspective side view of a surgical stapling instrument according to the invention;

FIG. 2 is an enlarged perspective distal-lateral view of a staple fastening assembly of the stapling instrument in FIG. 1;

Figure 3:
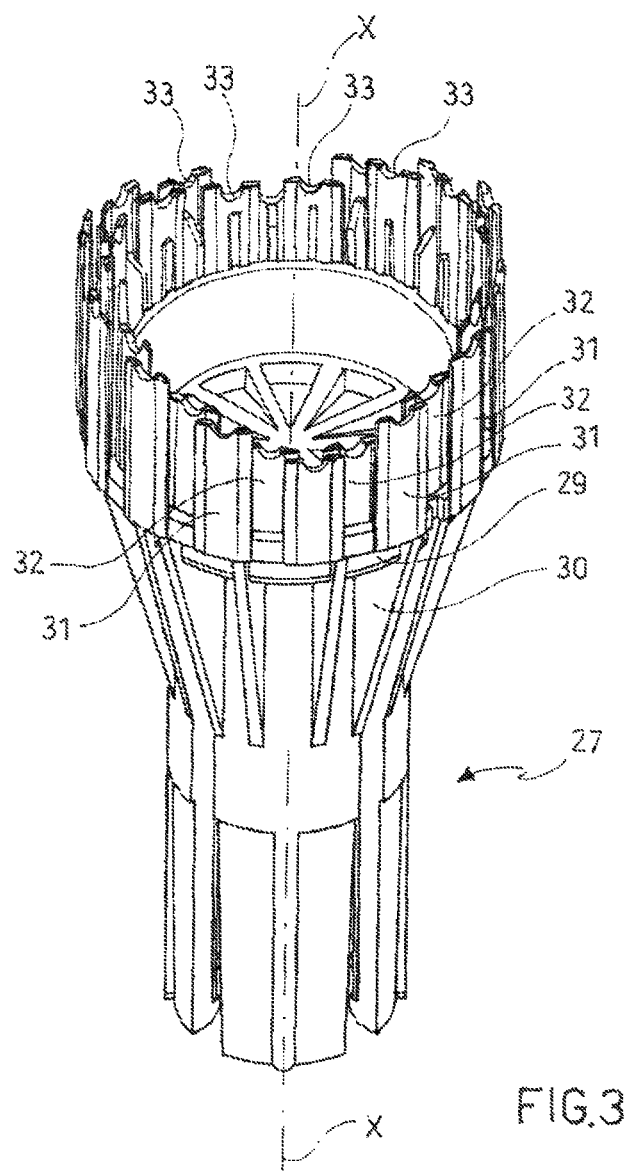
FIGS. 3 and 3A are a perspective distal-lateral view and a side view of a staple driving device of a surgical stapling instrument according to an embodiment of the invention.
Figure 3A:
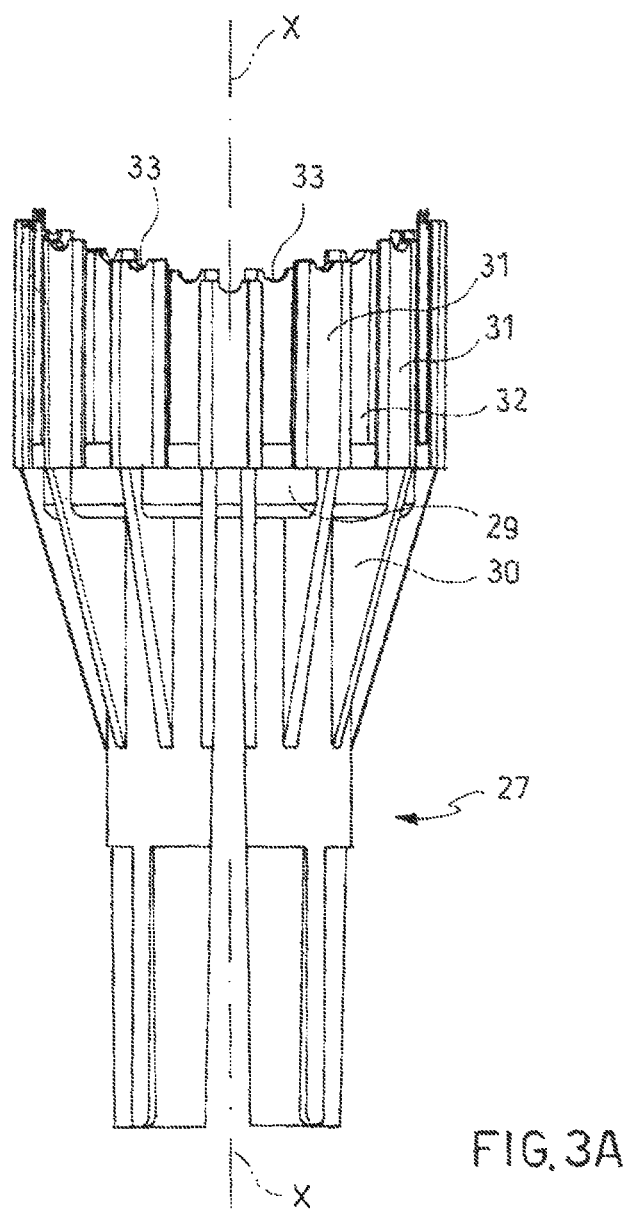
Figure 4:
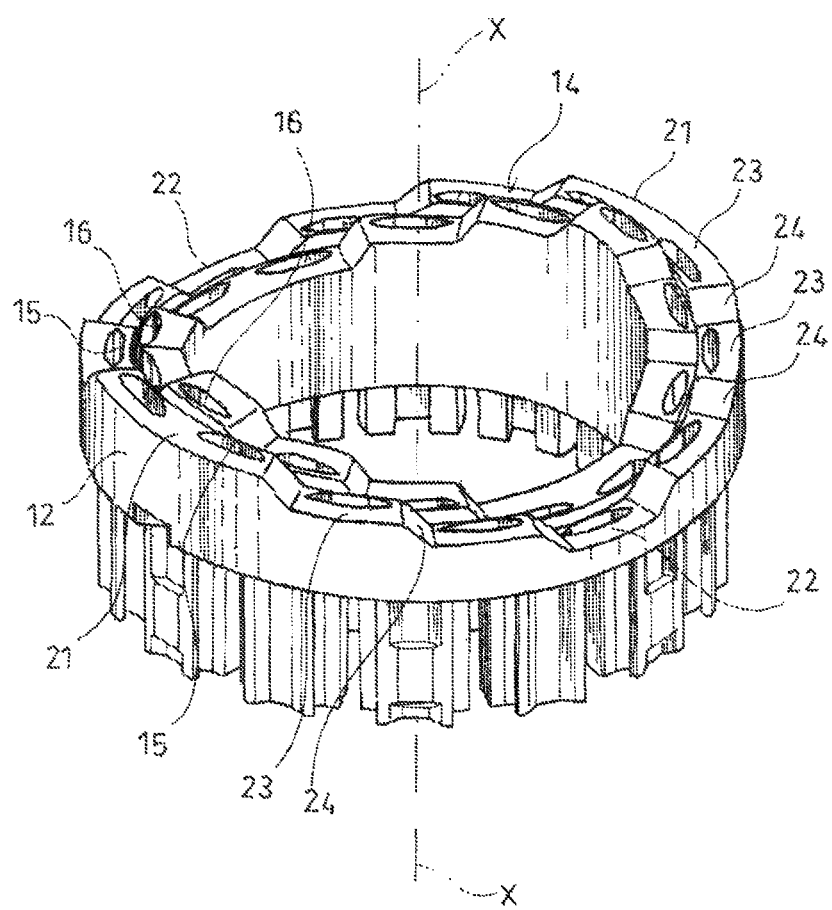
FIG. 4 is a perspective distal-lateral view of a staple cartridge device of a surgical stapling instrument according to an embodiment of the invention.
Figure 5A:
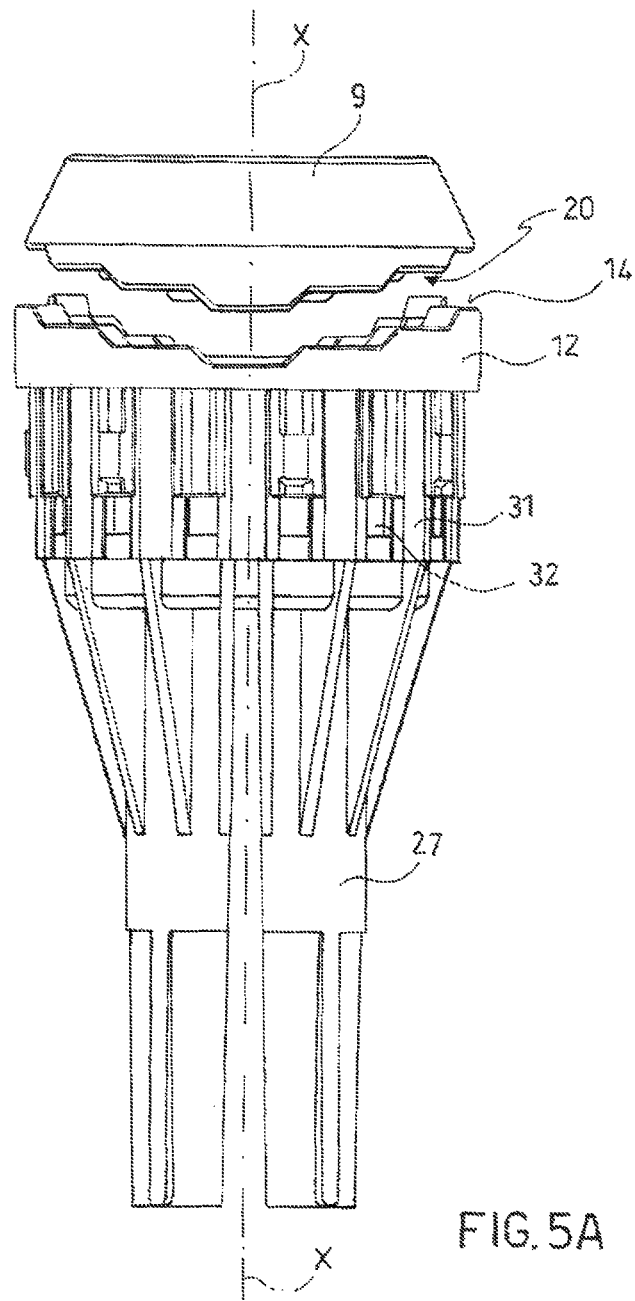
FIGS. 5A and 5B are side views of a staple fastening device of a surgical stapling instrument according to an embodiment of the invention in a retracted and protracted (staples expelled) configuration.
Figure 5B:
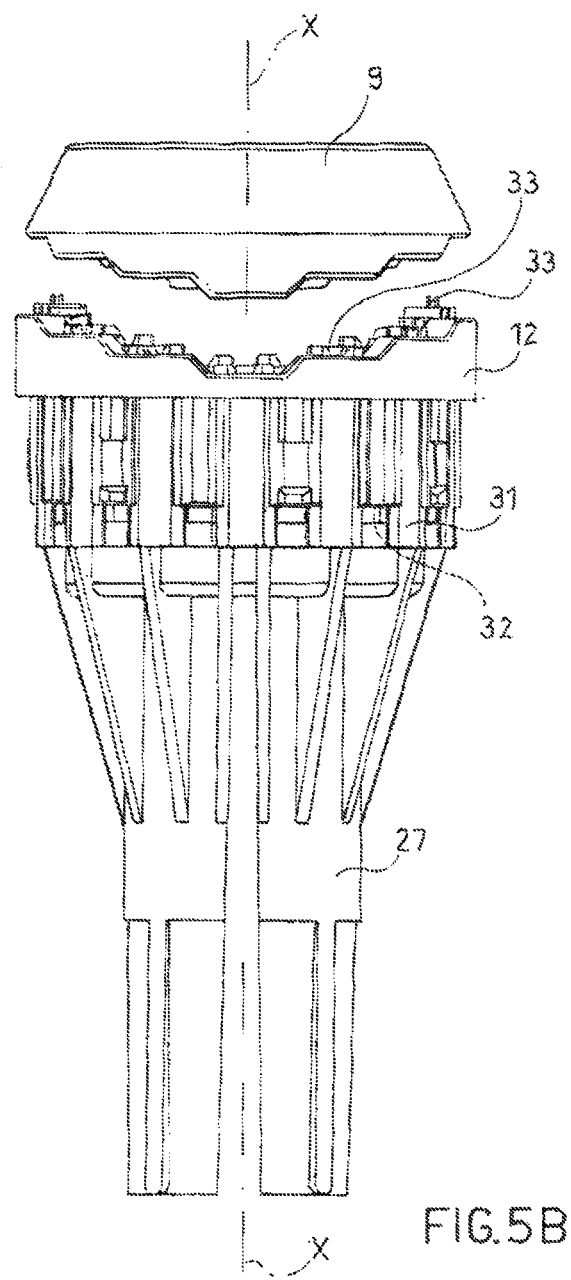

Turning to the figures, FIG. 1 shows an intraluminal surgical stapling instrument 1. The stapling instrument 1 comprises a frame having a body portion including a curved or straight shaft 2 and a handle 3. A staple fastening assembly 4 is preferably detachably mounted at the distal end of the shaft 2, in order to allow for removal of the staple fastening assembly from the shaft 2 and for replacement by another one, if desired.

An actuator trigger 5 is located in the proximal region of the stapling instrument 1. It can be swivelled towards handle 3 in order to "fire" the stapling instrument 1, i. e. for operating the staple driving device and the knife actuating device 27B of the internal mechanism of the stapling instrument. A rotatable adjusting knob 6 is provided for axially shifting a trocar shaft 7, in order to open or close the staple fastening assembly 4, i. e. in order to move the anvil of the stapling instrument 1.

The staple fastening assembly 4 includes a cartridge device 8 (which comprises, in the embodiment, two closed rows of staples) and an anvil 9. The anvil 9 is detachably connectable with a distal end 10 of the trocar shaft 7 which can be moved relative to the cartridge device 8, i.e. along the longitudinal axis X of the staple fastening assembly 4, in order to adjust the size of the gap between the anvil 9 and the cartridge device 8.

The cartridge device 8 comprises a housing 11 which contains the staples, a circular knife 27A, as well as components of a moving device (adapted to move the trocar shaft 7 relative to the cartridge device 8), a staple driving device (adapted to drive the staples out of the cartridge device 8 towards the anvil 9), and a knife actuating device 27B (adapted to move the knife towards the anvil 9). A distal end surface 14 of the cartridge device 8, i.e. the surface from which the staples exiting from the cartridge device 8 are expelled towards the anvil 9, is formed in a distal end portion 12 received by the circumferential wall of the housing 11.

As already explained above, the staple fastening assembly 4 can be detachably mounted on the shaft 2 of the stapling instrument by means of a coupling portion 13 provided at the proximal end region of the cartridge device 8. The terms "proximal" and "distal" relate to the view of the surgeon during normal use of the stapling instrument.

FIG. 2 is an enlarged distal lateral view of the staple fastening assembly 4. The distal end surface 14 of the staple cartridge device 8 comprises guide slots 15, 16 which receive the staples (not shown) and from which the staples are expelled towards the anvil 9 when the stapling instrument is "fired". These guide slots 15, 16 are arranged in two closed rows, thus defining a radially outer closed row 17 of staples (i.e. guide slots 15) and a radially inner closed row 18 of staples (i.e. guide slots 16).

As shown in FIG. 2, the guide slots 15 and hence the corresponding staples of the outer closed row 17 and the guide slots 16 and the corresponding staples of the inner closed row 18 are circumferentially staggered and preferably partially overlapping.

A staple guide part (hidden in the figures) is located below the distal end portion 12 and defines the guide slots 15 for guiding the staples of the outer closed row 17 and the guide slots 16 for guiding the staples of the inner closed row 18. Each of these guide slots 15, 16 houses one staple, the pointed ends of the staple facing the corresponding exit opening in the distal end surface 14. The staple guide part as well as the distal end portion 12 are preferably made of a medical grade resin by injection molding and may be manufactured integrally as one single component.

The circular knife 27A, which is not shown in the figures, is guided (in a conventional manner) at the inner periphery of the distal end portion 12 of the cartridge device 8. It is moved in distal direction when the stapling instrument is actuated, as usual with conventional circular staplers.

The anvil 9 comprises a proximally extending anvil shaft 19 which is configured to detachably engage the trocar shaft 7 and align the anvil 9 angularly with respect to the cartridge device 8. The anvil further comprises a proximally facing annular staple forming surface 20 defining a pair of staple-forming grooves for each staple in order to bend the pointed ends of the staple when it is pushed against the staple-forming surface 20 upon actuation of the staple drive device. The distal end surface 14 of the cartridge device and the staple forming surface 20 of the anvil constitute opposite tissue interfaces destined to contact directly and clamp the tissue in the gap between the cartridge device and the anvil.

Generally, the overall design and the mechanical components, drive mechanisms and safety features of the surgical stapling instrument are as in known circular stapling instruments (compare e.g. U.S. Pat. No. 5,309,927 and WO 01/54594); the three-dimensional shape of the tissue interfaces and staple lines and some details of the staple driving device, however, are different, as will be explained in the following.

The distal end surface 14 of the cartridge device and the staple forming surface 20 of the anvil have a generally wavy shape including two opposite peaks and two opposite valleys 22 angularly spaced at about 90°, wherein this two-peaks-two-valleys wave is obtained by a locally stepped or otherwise offset configuration which "oscillates" about the two-peaks-two-valleys wavy shape. Particularly, the stepped distal end surface 14 is composed of a series of lands 23 and risers 24, wherein the lands 23 are perpendicular to the longitudinal axis X of the staple fastening assembly 4 and the exit openings of the guide slots 15, 16 are defined in the lands 23. Analogously, also the staple forming surface 20 of the anvil is composed of a series of lands 25 and risers 26, wherein the lands 25 are perpendicular to the longitudinal axis X of the staple fastening assembly 4 and the staple forming recesses are defined in the lands 25.

In both the distal end surface 14 and the staple forming surface 20, the lands 23, 25 define with the risers 24, 26 an obtuse angle in order to reduce local tissue tensioning during clamping and stapling.

All staple guide slots 15, 16 extend in a substantially normal direction to the corresponding lands 23 and parallel with respect to the longitudinal axis X.

As a result, all staples housed in the guide slots are in parallel alignment with respect to the staple drive direction of the staple drive device (which will be described below) which coincides with the longitudinal axis X.

In accordance with the preferred embodiment, the staples are arranged in the cartridge device 8 along a wavy line including two opposite peaks and two opposite valleys angularly spaced at about 90° from the adjacent peaks, wherein the line along which the staples are arranged is substantially parallel to the distal end surface 14. In order to limit the diameter of the staple fastening assembly, the described wavy and stepped shape of the tissue interfaces deviates from a hypothetical circular reference shape in a plane perpendicular to the longitudinal axis X only in a direction normal to that plane, such that the projection of the distal end surface 14 and the staple forming surface 20, as well as the annular lines defined by the outer and inner staple rows 17, 18 onto that plane is circular.

As can be seen from the figures, according to the preferred embodiment, both peaks 21 have the same axial distance from a plane perpendicular to the longitudinal axis X. Analogously, also both valleys 22 have the same distance from a plane perpendicular to the longitudinal axis X. Preferably, the two-peaks-two-valleys wavy shape and the superimposed locally stepped shape of the distal end surface 14 and of the staple forming surface 20 are symmetrical with respect to a first plane defined by the longitudinal axis X and the two valley points 22 and with respect to a perpendicular second plane defined by the longitudinal axis X and the two peak points 21. This further reduces the longitudinal extension of the resulting anastomosis for a given target staple line length. The axial distance between the peaks 21 and the valleys 22 should be preferably less than 20 mm, even more preferably less than 10 mm, in order to reduce the risk of tissue necrosis due to blood supply insufficiency.

Although the foregoing description focused primarily on the geometry of the tissue interfaces and of the staple line geometry of the stapling instrument 1, in a preferred embodiment of the invention, the overall dimensioning of the surgical stapling instrument has been made in dependence from the above described wavy and stepped geometry, such that at least the external circumference of the anvil 9 is less or approximately equal to the total length of the tissue interface along the staple line. Best results have been obtained by selecting the ratio of the outside circumferential length of the anvil (and preferably also that of the staple cartridge device) to the staple line length in a range of about 0.95 to 1.02.

In stapler geometries different from a stepped double wave shape or stepped fishmouth shape of the present invention, experimentation has lead to the following selection of ratios between the staple line length and the external circumferential length of the anvil and, preferably, of the entire staple fastening assembly:

In circular staplers, in which the line defined by the closed row of staples has a stepped shape, leaving a median plane perpendicular to the longitudinal axis of the staple fastening assembly, the staple line has a greater length than the external circumference of the anvil or the staple fastening assembly and the ratio of the external circumference of the anvil or the staple fastening assembly to said staple line length is preferably in the range between 0.89 and 0.97.

In circular staplers, in which the line defined by the closed row of staples has a wavy shape, leaving a median plane perpendicular to the longitudinal axis of the staple fastening assembly, the staple line has a greater length than the external circumference of the anvil or the staple fastening assembly and the ratio of the external circumference of the anvil or the staple fastening assembly to said staple line length is preferably in the range between 0.95 and 1.02.

In circular staplers, in which the line defined by the closed row of staples has an elliptical shape, leaving a plane inclined to the longitudinal axis of the staple fastening assembly, the staple line has a greater length than the external circumference of the anvil or the staple fastening assembly and the ratio of the external circumference of the anvil or the staple fastening assembly to said staple line length is preferably in the range between 0.93 and 0.99.

In the embodiment, the cutting edge of the knife has approximately the same geometry of a two-peaks-two-valleys general created by a stepped or offset local geometry, as described above in relation with the tissue clamping surfaces 14, 20. The shape of the knife follows substantially the shape of the line along which the inner closed row of staples is arranged but has a slightly smaller diameter such as to cut along a inner circumference with respect to the inner staple row.

FIG. 3 shows the distal portion 27 of a staple driving device suitable for the stapling instrument which has been described so far. In the embodiment, this distal portion 27 is an integrally molded sleeve structure. It includes an actuator shaft 28 distally ending at a base 29 which is reinforced by means of ribs 30. The proximal end of the actuator shaft 28 is coupled to an actuating rod (not shown) inside the shaft 2 of the stapling instrument 1 when the staple fastening assembly 4 is mounted to the distal end of this shaft. When the instrument is "fired", i.e. when an actuating trigger located at the handle of the instrument is operated, the actuating rod is moved in distal direction, thus pushing the sleeve structure in distal direction, too.

For each staple, the staple driving device 27 comprises a pusher protruding in distal direction and parallel to the longitudinal axis X of the staple fastening assembly 4. The pushers are arranged in two rows, particularly an outer row of pushers 31 for the outer closed row 17 of staples and an inner row of pushers 32 for the inner closed row 18 of staples. In the assembled state of the staple fastening assembly 4, the outer pushers 31 are guided in the guide slots 15, whereas the inner pushers 32 are guided in the guide slots 16. As shown in FIG. 3, all pushers 31, 32 are parallel to each other and to the longitudinal axis X and their length is such that their distal end sides, i.e. the push surfaces 33 (abutting at the crowns of the corresponding staples) follow the two-peaks-two-valleys wavy shape described above with reference to the distal end surface 14. The push surfaces 33 are substantially perpendicular to the longitudinal axis X, thereby defining altogether a stepped or offset geometry "oscillating" about the wavy shape described above.

Figure 6A:
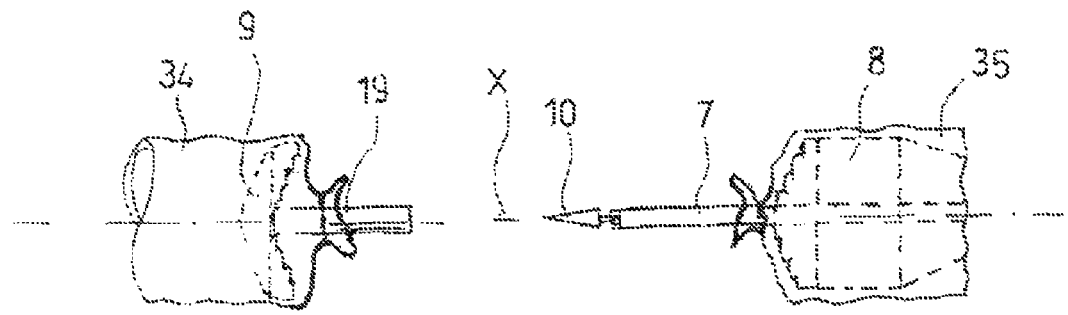
FIGS. 6A, 6B, 6C and 6D are side views of an approximating and stapling operation of the present invention.
Figure 6B:
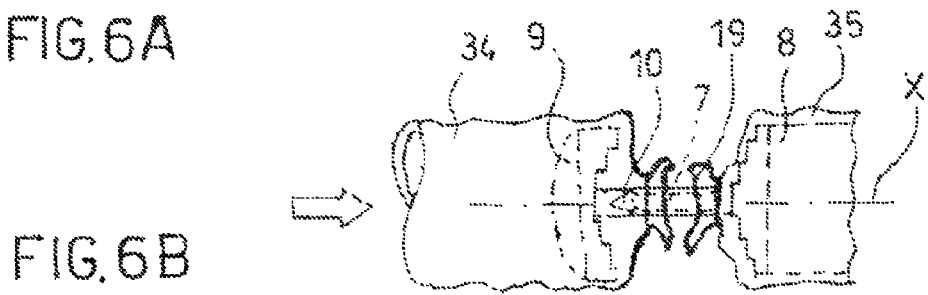
Figure 6C:
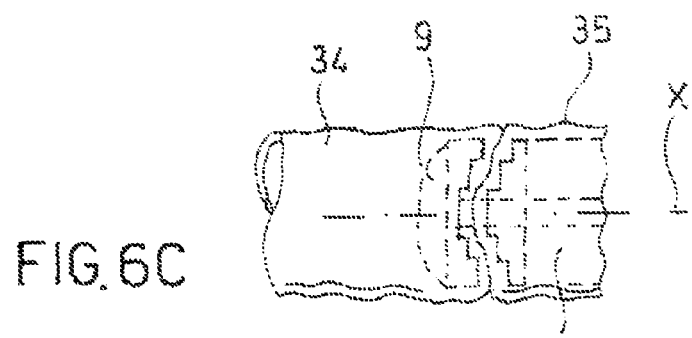
Figure 6D:
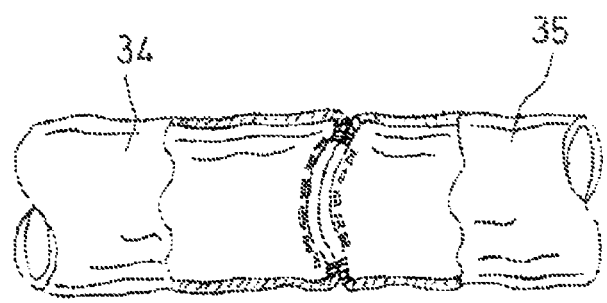

The operation of the stapling instrument 1 is illustrated in FIGS. 6A, 6B, 6C and 6D. FIG. 6A shows a situation in which the anvil 9 is already inserted in a distal lumen 34 and the proximal part of the staple fastening assembly 4 is placed inside the proximal lumen 35 to be joined in anastomosis with the distal lumen 34. The two lumens 34, 35 are attached to both the anvil shaft 19 and the trocar shaft 7, respectively. As seen in FIG. 6B, the anvil 9 is approximated to the trocar shaft 7 until the trocar shaft end 10 engages the anvil shaft 19. The angular alignment of the anvil with respect to the cartridge device is ensured e.g. by recesses formed in the anvil shaft 19 and corresponding serrations formed in the trocar shaft 7. After connecting the anvil to the trocar shaft 7, rotation of the adjusting knob 6 will approximate the anvil 9 and the cartridge device 8, thereby pulling the distal and proximal lumens 34, 35 towards each other and clamping them between the end surface 14 of the cartridge device and the staple-forming surface 20 of the anvil 9. In this phase, the tissue follows the shapes of the tissue clamping surfaces 14, 20 of the stapling instrument along the line(s) defined by the closed row(s) of staples.

When the instrument is fired, the staples are expelled almost simultaneously from the end surface of the cartridge device, penetrate the tissue and are clinched at the staple-forming surface of the anvil. Immediately afterwards, the cutting edge of the circular knife cuts the tissue held within the circumference of the staples. After firing, the distance between the anvil 9 and the cartridge device 8 is increased to an extent sufficient for releasing the anastomosis seam. Because of the combined wavy and stepped geometry of the end surface 14 of the cartridge device and the staple-forming surface 20 of the anvil, the stapled seam has a greater length than comparable stapled seams obtainable by means of known circular staplers of the same outer diameter and at the same time a reduced longitudinal extension. Consequently, retraction of the instrument is easier, the risk of tissue trauma and of post-operative complications is reduced.

Although a preferred embodiment of the invention has been described in detail, it is not the intention of the applicant to limit the scope of the claims to such particular embodiment, but to cover all modifications and alternative constructions falling within the scope of the invention.

What is claimed is:
1. A surgical stapling instrument (1) comprising:
a frame having a body portion (2) and a handle (3),
a staple fastening assembly (4) in the distal region of said instrument, the staple fastening assembly (4) including a cartridge device (8) which comprises two rows (17, 18) of staples and defines a distal end surface (14), and an anvil (9) which defines a proximal staple forming surface (20) substantially matching the distal end surface (14) and which is movable relative to the cartridge device (8) and adapted to cooperate with the cartridge device (8) for forming the ends of the staples exiting from the cartridge device (8),
a moving device adapted to move the anvil (9) relative to the cartridge device (8) along a longitudinal axis (X) of the staple fastening assembly (4),
a staple driving device (27) adapted to drive the staples out of the cartridge device (8) towards the anvil (9),
wherein said distal end surface (14) and said staple forming surface (20) have a wavy shape including two opposite peaks (21) and two opposite valleys (22), each of said two opposite valleys (22) being angularly spaced at about 90° from the directly bordering peaks (21), and wherein said two-peaks-two-valleys wavy shape is formed by a stepped configuration of said surfaces (14, 20),
wherein the distal end surface (14) forms:
exit openings of a radially outer row of staple guide slots (15) in a plurality of different planes perpendicular to the longitudinal axis (X), and
exit openings of a radially inner row of staple guide slots (16) in a plurality of different planes perpendicular to the longitudinal axis (X).

2. The surgical stapling instrument (1) of claim 1, wherein the staple driving device (27) comprising at least a first and second pusher in a row (31, 32), the first and second pusher having different heights.

3. The surgical stapling instrument (1) of claim 2, wherein the first and second pusher being configured to abut a portion of a respective staple.

4. The surgical stapling instrument (1) of claim 1, wherein the staple driving device (27) comprises a first row of pushers (31), wherein at least a one pusher in the first row of pushers (31) comprises a different height than at least one other pusher in the first row of pushers (31).

5. The surgical instrument (1) of claim 4, wherein the staple driving device (27) comprises a second row of pushers (32), wherein at least a one pusher in the second row of pushers (32) comprises a different height than at least one other pusher in the second row of pushers (32).

6. The surgical instrument (1) of claim 5, wherein the first row of pushers (31) and second row of pushers (32) each form a respective, closed, circular row.

7. The surgical instrument (1) of claim 6, the second row of pushers (32) is parallel and inside the first row of pushers (31).

8. The surgical instrument (1) of claim 5, wherein each pusher in the first row of pushers (31) is configured to abut a respective staple in a first row of the two rows of staples; and each pusher in the second row of pushers (32) is configured to abut a respective staple in a second row of the two rows of staples.

9. A surgical stapling instrument (1) comprising:
a frame having a body portion (2) and a handle (3),
a staple fastening assembly (4) in the distal region of said instrument, the staple fastening assembly (4) including a cartridge device (8) which comprises two rows (17, 18) of staples and defines a distal end surface (14), and an anvil (9) which defines a proximal staple forming surface (20) substantially matching the distal end surface (14) and which is movable relative to the cartridge device (8) and adapted to cooperate with the cartridge device (8) for forming the ends of the staples exiting from the cartridge device (8),
a moving device adapted to move the anvil (9) relative to the cartridge device (8) along a longitudinal axis (X) of the staple fastening assembly (4), a staple driving device (27) adapted to drive the staples out of the cartridge device (8) towards the anvil (9), wherein the staple driving device (27) comprising at least a first and second pusher in a circular row (31, 32), the first and second pusher having different heights, wherein said distal end surface (14) and said staple forming surface (20) have a wavy shape including two opposite peaks (21) and two opposite valleys (22), each of said two opposite valleys (22) being angularly spaced at about 90° from the directly bordering peaks (21), and wherein said two-peaks-two-valleys wavy shape is formed by a stepped configuration of said surfaces (14, 20), wherein the distal end surface (14) forms:

exit openings of a radially outer row of staple guide slots (15) in a plurality of different planes perpendicular to the longitudinal axis (X), and exit openings of a radially inner row of staple guide slots (16) in a plurality of different planes perpendicular to the longitudinal axis (X).

10. The surgical stapling instrument (1) of claim 9, wherein the first and second pusher being configured to abut a portion of a respective staple.

11. A surgical stapling instrument (1) comprising:

a frame having a body portion (2) and a handle (3), a staple fastening assembly (4) in the distal region of said instrument, the staple fastening assembly (4) including a cartridge device (8) which comprises two rows (17, 18) of staples and defines a distal end surface (14), and an anvil (9) which defines a proximal staple forming surface (20) substantially matching the distal end surface (14) and which is movable relative to the cartridge device (8) and adapted to cooperate with the cartridge device (8) for forming the ends of the staples exiting from the cartridge device (8), a moving device adapted to move the anvil (9) relative to the cartridge device (8) along a longitudinal axis (X) of the staple fastening assembly (4), a staple driving device (27) adapted to drive the staples out of the cartridge device (8) towards the anvil (9), wherein the staple driving device (27) comprises a first row of pushers (31), wherein at least a one pusher in the first row of pushers (31) comprises a different height than at least one other pusher in the first row of pushers (31), wherein said distal end surface (14) and said staple forming surface (20) have a wavy shape including two opposite peaks (21) and two opposite valleys (22), each of said two opposite valleys (22) being angularly spaced at about 90° from the directly bordering peaks (21), and wherein said two-peaks-two-valleys wavy shape is formed by a stepped configuration of said surfaces (14, 20), wherein the distal end surface (14) forms:

exit openings of a radially outer row of staple guide slots (15) in a plurality of different planes perpendicular to the longitudinal axis (X), and exit openings of a radially inner row of staple guide slots (16) in a plurality of different planes perpendicular to the longitudinal axis (X).

12. The surgical instrument (1) of claim 11, wherein the staple driving device (27) comprises a second row of pushers (32), wherein at least a one pusher in the second row of pushers (32) comprises a different height than at least one other pusher in the second row of pushers (32).

13. The surgical instrument (1) of claim 12, wherein the first row of pushers (31) and second row of pushers each form a respective, closed, circular row.

14. The surgical instrument (1) of claim 13, wherein the second row of pushers (32) is parallel and inside the first row of pushers (31).

15. The surgical instrument (1) of claim 12, wherein each pusher in the first row of pushers (31) is configured to abut a respective staple in a first row of the two rows of staples, and each pusher in the second row of pushers (32) is configured to abut a respective staple in a second row of the two rows of staples.

\* \* \* \* \*